United States Patent

Lee et al.

[11] Patent Number: 5,510,379
[45] Date of Patent: Apr. 23, 1996

[54] SULFONATE ACAT INHIBITORS

[75] Inventors: Helen T. Lee, Ann Arbor; Joseph A. Picard, Canton; Drago R. Sliskovic, Ypsilanti, all of Mich.

[73] Assignee: Warner-Lambert Company, Morris Plains, N.J.

[21] Appl. No.: 359,144

[22] Filed: Dec. 19, 1994

[51] Int. Cl.$^6$ .................. C07C 309/69; C07C 309/70; A61K 31/095; C07D 487/04

[52] U.S. Cl. .................. 514/517; 514/510; 514/513; 514/300; 514/404; 514/312; 514/457; 514/341; 514/256; 514/252; 514/314; 514/246; 514/248; 514/259; 514/274; 514/351; 514/387; 514/445; 514/443; 514/473; 514/470; 514/469; 514/247; 514/255; 514/424; 514/407; 514/372; 514/365; 514/376; 514/380; 514/384; 514/359; 514/392; 514/386; 514/367; 514/418; 514/415; 514/311; 514/309; 514/307; 558/50; 558/49; 558/52; 546/122; 546/153; 546/294; 546/157; 546/172; 546/141; 546/147; 546/146; 548/370.1; 548/370.4; 548/550; 548/551; 548/213; 548/187; 548/228; 548/229; 548/243; 548/255; 548/264.4; 548/324.1; 548/166; 548/178; 548/180; 548/251; 548/486; 548/484; 548/510; 548/265.4; 549/471; 549/399; 549/410; 549/65; 549/66; 549/52; 549/51; 549/479; 549/466; 544/215; 544/237; 544/235; 544/283; 544/315; 544/319; 544/298; 544/239; 544/408

[58] Field of Search .................. 558/49, 50; 514/517, 514/510

[56] References Cited

U.S. PATENT DOCUMENTS 4,567,004  1/1986  Blank et al. .................. 260/465 R Primary Examiner—Cecilia Tsang
Assistant Examiner—King Lit Wong
Attorney, Agent, or Firm—Charles W. Ashbrook; Todd M. Crissey

[57] ABSTRACT

β-Carboxy sulfonates of the formula

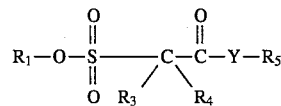

wherein $R_1$ is aryl, $R_3$ and $R_4$ are hydrogen or alkyl, Y is -O-, -S-, or -NR$_2$-, and $R_5$ is alkyl or aryl are potent inhibitors of the enzyme acyl CoA:cholesterol acyltransferase (ACAT) and are thus useful for treating hypercholesterolemia and atherosclerosis.

13 Claims, No Drawings

SULFONATE ACAT INHIBITORS

BACKGROUND OF THE INVENTION

This invention provides new chemical compounds characterized as being β-carboxy sulfonates. The compounds inhibit acyl-CoA: cholesterol acyltransferase (ACAT), the enzyme responsible for the esterification of dietary cholesterol. Such agents thus decrease the absorption of dietary cholesterol and therefore provide a therapy for individuals with hypercholesterolemia and atherosclerosis.

High levels of cholesterol have been associated with heightened risk for development of several disease states, most notably coronary heart disease. A great deal of effort has been devoted to finding ways to lower cholesterol levels in biological systems. The approach of lowering cholesterol intake by modifying diet has met with only limited success. The ACAT enzyme is known to catalyze the esterification of dietary cholesterol, and has been implicated in several aspects of the atherosclerotic process in animals. One approach to lowering cholesterol then is to inhibit the ACAT enzyme. While several ACAT inhibitors have been identified (see for example EP 0570245), the need continues to identify and develop new ACAT inhibitors having improved therapeutic properties.

An object of this invention is therefore to provide a new series of compounds which are β-carboxy sulfonate derivatives and which have demonstrated excellent ACAT inhibitory properties. Another object is to provide pharmaceutical formulations comprising the sulfonates and a carrier or excipient, and a method for inhibiting the ACAT enzyme by administering a compound of the invention.

SUMMARY OF THE INVENTION

This invention concerns new compounds which are β-carboxy sulfonates and which inhibit the ACAT enzyme.

The compounds of the invention have the Formula I

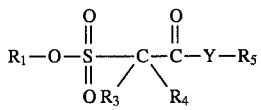

wherein $R_1$ is selected from
(a) phenyl which is unsubstituted or is substituted with from 1 to 3 substituents selected from
$C_1$–$C_4$ alkyl,
$C_1$–$C_4$ alkoxy,
$C_1$–$C_4$ alkyl thio,
hydroxy,
halo,
nitro,
cyano,
trifluoromethyl,
-COOH,
-COOalkyl wherein alkyl has from 1 to 4 carbon atoms and which is straight or branched,
-$(CH_2)_m NR_x R_y$ wherein m is 0 or 1, and each of $R_x$ and $R_y$ is independently hydrogen or $C_1$–$C_4$ alkyl;
(b) 1- or 2-naphthyl which is unsubstituted or substituted with from 1 to 3 substituents selected from
$C_1$–$C_4$ alkyl,
$C_1$–$C_4$ alkoxy,
$C_1$–$C_4$ alkylthio,
hydroxy,
halo,
nitro,
cyano,
trifluoromethyl,
-COOH,
-COOalkyl wherein alkyl has from 1 to 4 carbon atoms and which is straight or branched,
-$(CH_2)_m NR_x R_y$ wherein m is 0 or 1, and each of $R_x$ and $R_y$ is independently hydrogen or $C_1$–$C_4$ alkyl;
(c) the group

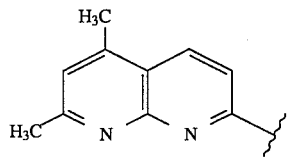

(d) the group

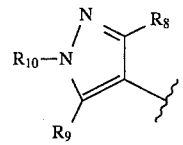

wherein $R_8$ and $R_9$ independently are $C_1$–$C_4$ alkyl or phenyl, and R10 is a straight or branched hydrocarbon group having from 1 to 18 carbon atoms which is saturated or is unsaturated containing one double bond or two nonadjacent double bonds; phenyl; phenyl substituted with from 1 to 3 substituents selected from
$C_1$–$C_4$ alkyl,
$C_1$–$C_4$ alkoxy,
hydroxy,
halo,
nitro,
cyano,
trifluoromethyl,
-COOH,
-COOalkyl wherein alkyl has from 1 to 4 carbon atoms and is straight or branched,
-$(CH_2)_m NR_x R_y$ wherein m, $R_x$, and $R_y$ are as defined above; or
a heterocyclic group selected from 2-, 3-, or 4-pyridyl, 2-, 4-, or 5-pyrimidinyl, 2-, or 3-pyrazinyl, 2-, 3-, 4-, 5-, 6-, 7-, or 8-quinolinyl, 3- or 4-pyridazinyl, and the N-oxides thereof;
(e) the group

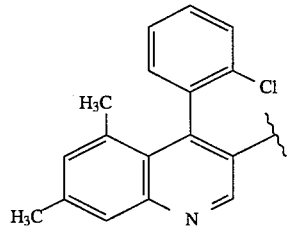

(f) a straight or branched hydrocarbon group having from 1 to 18 carbon atoms which is saturated or is unsaturated containing one double bond or two nonadjacent double bonds;

(g) a cycloalkyl group having from 3 to 10 carbon atoms;

(h) the group

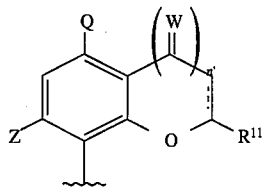

wherein — denotes a single or double bond; Q and Z are each independently hydrogen, $C_1$–$C_4$ alkyl, $C_1$–$C_4$ alkoxy, or halo;

W is oxygen or two hydrogen atoms;

$R^{11}$ is hydrogen or $C_1$–$C_4$ alkyl, and n' is 0 or 1;

(i) is selected from the group

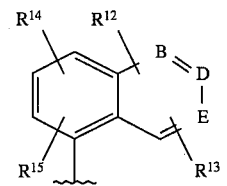

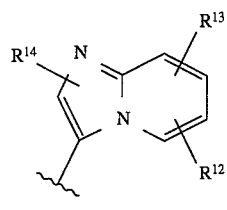

and

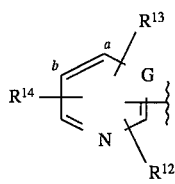

wherein $R^{12}$, $R^{13}$, $R^{14}$, and $R^{15}$ are each independently hydrogen, halo, $C_1$–$C_4$ alkyl, $C_1$–$C_4$ alkoxy, $C_1$–$C_4$ alkylthio, cycloalkylthio of 5 to 7 carbon atoms, phenylalkylthio in which alkyl is 1 to 4 carbon atoms, substituted phenylthio, heteroarylthio, or heteroaryloxy; and B, D, E, and G are nitrogen or carbon where one or more of B, D, and E is nitrogen; with the proviso that when G =N, the group is attached to the nitrogen atom of Formula I at the four or five position of the pyrimidine ring (a and b); or (j) a 5- or 6-membered monocyclic or fused bicyclic heterocycle containing from 1 to 4 heteroatoms selected from nitrogen, oxygen, and sulfur; $R_3$ and $R_4$ independently are $C_3$–$C_6$ cycloalkyl, hydroxy-$C_1$–$C_4$ alkyl, $C_1$–$C_4$ alkoxy, hydrogen, $C_1$–$C_4$ alkyl, phenyl, 1- or 2-naphthyl, or phenyl or naphthyl substituted with from 1 to 3 substituents selected from $C_1$–$C_4$ alkyl, $C_1$–$C_4$ alkoxy, $C_1$–$C_4$ alkylthio, halo, nitro, cyano, trifluoromethyl, phenyl, or $C_3$–$C_8$ cycloalkyl, or $R_3$ and $R_4$ taken together with the carbon to which they are attached complete a $C_3$–$C_8$ carbocyclic ring;

Y is -O-, -S-, or -$NR_2$-, wherein $R_2$ is hydrogen, $C_1$–$C_4$ alkyl, phenyl, $C_1$–$C_4$ alkyl, phenyl, wherein the phenyl may be substituted with 1, 2, or 3 groups selected from $C_1$–$C_4$ alkyl, $C_1$–$C_4$ alkoxy, $C_1$–$C_4$ alkylthio, hydroxy, halo, nitro, cyano, trifluoromethyl, and COOH;

$R_5$ is $R_6$, $C_1$–$C_{20}$ alkyl, $C_2$–$C_{20}$ alkenyl, $C_2$–$C_{20}$ alkynyl and alkyl, alkenyl and alkenyl substituted with one or two groups defined by $R_6$, where $R_6$ is hydrogen, $C_3$–$C_6$ cycloalkyl, phenyl, 1- or 2- naphthyl, and phenyl and naphthyl substituted with from 1 to 3 substituents selected from:

$C_1$–$C_4$ alkyl, $C_1$–$C_4$ alkoxy, $C_1$–$C_4$ alkylthio, phenyl, hydroxy, halo, nitro, cyano, trifluoromethyl,

-COOH,

-COOalkyl wherein alkyl has from 1 to 4 carbon atoms and which is straight or branched, -$(CH_2)_m NR_x R_y$, wherein m is 0 or 1, and each of $R_x$ and $R_y$ is hydrogen or a straight chain alkyl group having 1 to 4 carbon atoms; and $R_6$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with amino, halo, nitro, hydroxy, cyano, trifluoromethyl, or an alkyl group having from 1 to 20 carbon atoms and the N-oxides thereof.

Preferred compounds of the invention have the Formula II

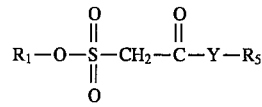

wherein $R_1$, Y, and $R_5$ are as defined above. Further preferred are those of the above formula in which Y is -O-, -S-, or -NH-, and especially where Y is -NH-. Additionally preferred are compounds of Formula II wherein $R_1$ is phenyl or substituted phenyl, Y is -O- or S, and $R_5$ is $C_6$–$C_{20}$ alkyl, phenyl, or substituted phenyl. Preferred substituted phenyl groups are di- and trialkyl, such as diisopropyl and triisopropyl.

Particularly preferred compounds have Formula II wherein:

A. $R_1$ is phenyl or phenyl substituted with 1 or 2 $C_1$–$C_4$ alkyl groups;

A(1) Y is NH and $R_5$ is $C_6$–$C_{20}$ alkyl;

A(2) Y is NH and $R_5$ is phenyl or phenyl substituted with 1 or 2 $C_1$–$C_4$ alkyl or $C_1$–$C_4$ alkoxy groups;

A(3) Y is NH and $R_5$ is pyridyl or pyridyl substituted with 1 or 2 $C_1$–$C_4$ alkyl groups;

A(4) Y is S and $R_5$ is $C_6$–$C_{20}$ alkyl;

A(5) Y is O and $R_5$ is $C_6$–$C_{20}$ alkyl;

A(6) Y is O and $R_5$ is phenyl or phenyl substituted with 1 or 2 $C_1$–$C_4$ alkyl groups;

A(7) Y is NH and $R_5$ is tetrazolyl or tetrazolyl substituted with a $C_6$–$C_{20}$ alkyl group;

B. $R_1$ is phenyl substituted with 1, 2, or 3 $C_1$–$C_4$ alkoxy groups;

B(1) Y is NH and $R_5$ is phenyl or phenyl substituted with 1, 2, or 3 $C_1$–$C_4$ alkoxy groups;

B(2) Y is NH and $R_5$ is $C_6$–$C_{20}$ alkyl;

B(3) Y is S and $R_5$ is $C_6$–$C_{20}$ alkyl;

B(4) Y is O and $R_5$ is $C_6$–$C_{20}$ alkyl;

B(5) Y is O and $R_5$ is phenyl or phenyl substituted with 1, 2, or 3 $C_1$–$C_4$ alkoxy groups;

C. $R_1$ is 1- or 2-naphthyl or 1- or 2-naphthyl substituted with 1, 2, or 3 groups selected from $C_1$–$C_4$ alkyl or $C_1$–$C_4$ alkoxy;

C(1) Y is NH and $R_5$ is $C_6$–$C_{20}$ alkyl, phenyl, or phenyl substituted with 1, 2, or 3 groups selected from $C_1$–$C_4$ alkyl or $C_1$–$C_4$ alkoxy;

C(2) Y is S and $R_5$ is $C_6$–$C_{20}$ alkyl;

C(3) Y is O and $R_5$ is $C_6$–$C_{20}$ alkyl, phenyl, tetrazolyl, or phenyl substituted with 1, 2, or 3 $C_1$–$C_4$ alkyl groups;

C(4) Y is O and $R_5$ is hydrogen;

D. $R_1$ is $C_1$–$C_{20}$ alkyl;

D(1) Y is O and $R_5$ is phenyl or phenyl substituted with 1 or 2 $C_1$–$C_4$ alkyl groups;

D(2) Y is S and $R_5$ $C_6$–$C_{20}$ alkyl;

E. $R_1$ is pyridyl or pyridyl substituted with 1 or 2 $C_1$–$C_4$ alkyl groups;

E(1) Y is O or S and $R_5$ $C_6$–$C_{20}$ alkyl;

F. $R_1$ is 4,6-dialkylpyridin-5-yl;

F(1) Y is NH and $R_5$ $C_6$–$C_{20}$ alkyl;

F(2) Y is S and $R_5$ is phenyl or phenyl substituted with 1, 2, or 3 $C_1$–$C_4$ alkyl groups;

G. $R_1$ is 4-(2-chlorophenyl)-5,7-dimethylquinolin-2-yl;

G(1) Y is O and $R_5$ is $C_6$–$C_{20}$ alkyl;

G(2) Y is NH and $R_5$ is phenyl or phenyl substituted with 1, 2, or 3 $C_1$–$C_4$ alkoxy groups;

G(3) Y is S and $R_5$ is $C_2$–$C_{20}$ alkenyl;

The most preferred compounds of the invention are defined by Formula II when $R_1$ is phenyl or substituted phenyl, Y is -NH- and $R_5$ is phenyl or dialkylphenyl.

Also provided by this invention are pharmaceutical formulations comprising a compound of Formula I together with a pharmaceutically acceptable excipient, carrier, or diluent. Preferred formulations are those having a compound of Formula II or any of the preferred compounds of A-G as the active ingredient. The invention also provides a method of treating hypercholesterolemia, atherosclerosis, and inhibiting the ACAT enzyme, comprising administering to a subject an effective amount of a compound of Formula I to treat such conditions and to inhibit such enzyme.

DETAILED DESCRIPTION

The compounds of this invention are named as sulfonates, and more specifically as carbonylmethyl sulfonates. For example, the invention compound of the formula

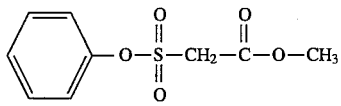

will be named phenyl methoxycarbonylmethyl sulfonate.

Pharmaceutically acceptable salts of the compounds of Formula I are also included as a part of the present invention. Suitable acids for forming salts of the compounds of Formula I containing a basic group such as amino or pyridyl include, but are not necessarily limited to acetic, benzoic, benzenesulfonic, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. Additional acids for use to form acid salts of the compounds of Formula I include, but are not necessarily limited to, those acids found in Tables 3 and 4 of Grant & Hackh's Chemical Dictionary, Fifth Edition, 1987:11–13. The acid addition salts are formed by procedures well known in the art.

Certain compounds of the present invention may also exist in different isomeric forms, specifically stereoisomeric forms, by virtue of the presence of asymmetric centers in the compound. The present invention contemplates all stereoisomers that may be obtained, if desired, by methods known in the art as, for example, the separation of stereoisomers by chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

In Formula I, $R_5$ can be $C_1$–$C_{20}$ alkyl, $C_2$–$C_{20}$ alkenyl, or $C_2$–$C_{20}$ alkynyl. Each of these groups can have one or two groups defined by $R_6$ attached, for example a substituted or unsubstituted phenyl, or a substituted or unsubstituted naphthyl, or a cycloalkyl such as cyclopropyl can be attached to the carbon chain. Illustrative examples of straight or branched saturated hydrocarbon chains having from 1 to 20 carbon atoms include methyl, ethyl, 2-cyclobutyl-2-phenylethyl, n-propyl, isopropyl, n-butyl, iso-butyl, tert-butyl, n-pentyl, 5-phenylpentyl, 2-cyclopropyl-5-phenylpentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon alkenyl chains having from 2 to 20 carbon atoms and having one double bond or two nonadjacent double bonds include ethenyl, 2-propenyl, 2-butenyl, 4-cyclobutyl-2-butenyl, 3-pentenyl, 2-octenyl, 5-nonenyl, 4-undecenyl, 5-heptadecenyl, 3-octadecenyl, 9-octadecenyl, 9-phenyl-9-octadecenyl, 2,2-dimethyl-11-eicosenyl, 9,12-octadecadienyl, and hexadecenyl. Typical alkynyl groups are those having from 2 to 20 carbon atoms with one triple bond or two monoadjacent triple bonds and include 2-octynyl, 5-hepta-3-decynyl, and 4-phenyl-2-butynyl.

$R_1$ in Formula I includes phenyl substituted with 1, 2, or 3 groups such as $C_1$–$C_4$ alkyl, $C_1$–$C_4$ alkoxy and $C_1$–$C_4$ alkylthio. Straight or branched $C_1$–$C_4$ alkyl groups include methyl and isopropyl. Straight or branched alkoxy groups having 1 to 4 carbon atoms include methoxy, ethoxy, n-propoxy, n-butoxy, and isopropoxy. $C_1$–$C_4$ alkylthio includes groups such as methylthio, ethylthio, isopropylthio, and the like.

Cycloalkyl groups having from 3 to 10 carbon atoms which $R_1$ and $R_4$ may represent include cyclopropyl, cyclobutyl, cyclopentyl, cyclohexyl, cycloheptyl, and cyclooctyl.

Halo is fluoro, chloro, bromo, or iodo, but preferably bromo and chloro.

A 5- or 6-membered monocyclic or fused bicyclic heterocycle is a monocyclic or fused bicyclic aromatic ring containing at least one to four heteroatoms in at least one ring, such as nitrogen, oxygen, or sulfur, or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycles containing a nitrogen atom.

More specifically, such a heterocycle may be a 2- or 3-thienyl; 2- or 3-furanyl; 2-, 3-, or 4-pyridyl or 2-, 3-, or 4-pyridinyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3- or 5-(1,2,4)-triazolyl; 4- or 5-(1,2,3)-triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

A preferred embodiment of this invention includes compounds having the formula

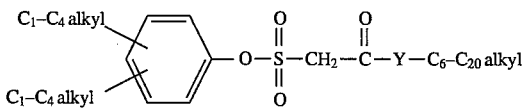

where Y is O, S, or NH, and especially NH.

Also preferred are compounds of the formula

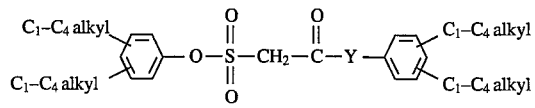

where Y is O, S, or NH, and especially NH.

Another class of compounds provided by the invention have the formula

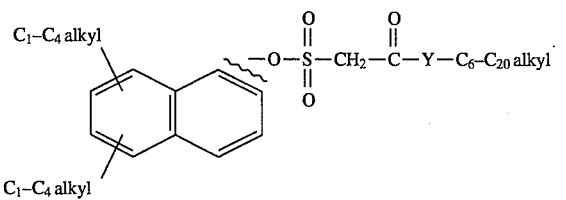

Another class of invention compounds have the formula

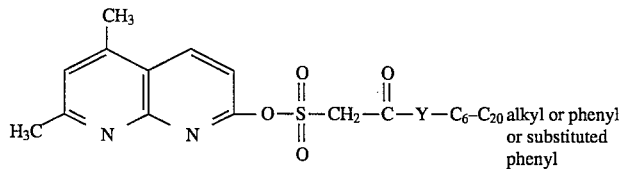

where Y is O, S, or NH, and substituted phenyl is phenyl having 1, 2, or 3 substituents as defined above.

Another preferred group of compounds of the invention have the formula

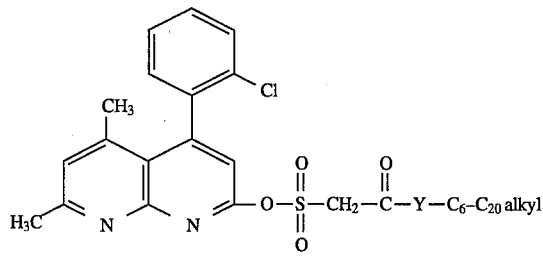

Still other compounds of the invention have the formula

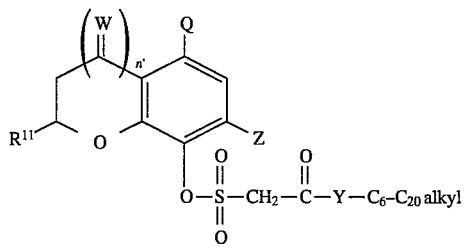

wherein $R_2$, $R_3$, $R_4$, $R_{11}$, W, n', Q, and Z are as defined above, and Y is O, S, or NH.

The compounds of this invention are prepared by any of several synthetic routes utilizing routine methodology well known to those skilled in the art of organic chemistry. The compounds are prepared from readily available starting materials and reactants.

In a preferred embodiment, compounds of Formula II

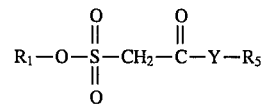

are prepared by reacting an alcohol, thiol, or amine of the formula H-Y-$R_5$ with an sulfonic acetyl halide of the formula

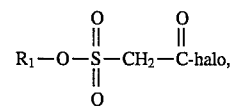

where $R_1$ is as defined above and halo is preferably bromo or chloro. The sulfonic acetyl halides are readily prepared by starting with a sulfonic acetic acid, which can be reacted with an alcohol to give the corresponding sulfonic acetic acid ester, which reacts with a halogenating agent to give the corresponding sulfonyl halide. The sulfonyl halide is reacted with an alcohol $R_1OH$ to provide the corresponding sulfonic acetic acid ester. The ester is readily hydrolyzed to the acid, which is then converted to the corresponding sulfonic acetyl halide. The above reaction is depicted by the general scheme of Chart I as follows:

CHART I

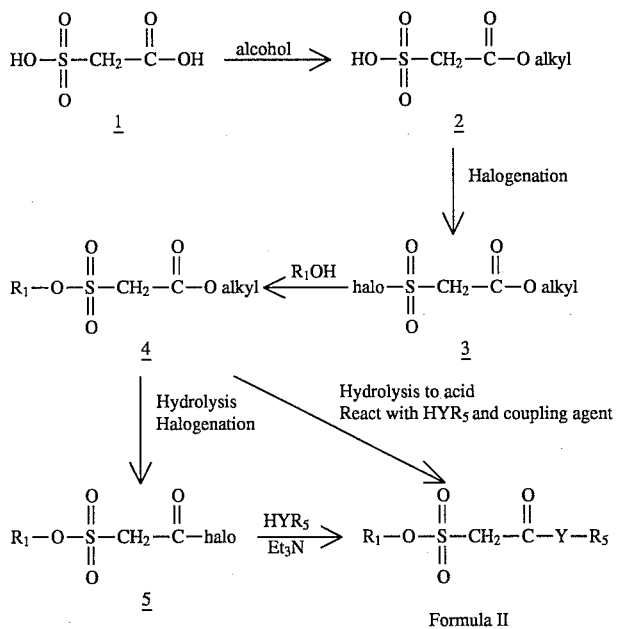

In a typical synthesis, for example, sulfoacetic acid (1) is reacted with ethanol at about 50° C. for 2 hours to give the acetic acid ethyl ester (2 where alkyl is ethyl). The ethyl ester is reacted with a halogenating agent such as phosphorus oxychloride to give the corresponding sulfonylchloride (3 where halo is chloro).

The sulfonyl chloride 3 is reacted with an alcohol (preferably a phenol, especially a di- or trisubstituted phenol) to produce the sulfonate acetic acid ester 4. The ester 4 is readily converted to an acid halide by first hydrolyzing the ester, for instance by reaction with an alkaline base such as sodium hydroxide or potassium hydroxide to give the sulfonate acetic acid, and then reacting the acid with a halogenating agent such as oxalyl chloride or the like to give an acid halide 5. The acid chloride 5 is reacted with about an equimolar quantity of an alcohol, thiol, or amine of the formula $HYR_5$ to give the invention compound of Formula II. This latter reaction typically is carried out in an unreactive organic solvent such as methylene chloride or toluene, and normally is complete in about 2 to 24 hours when carried out at about 20°–60° C. The product of Formula II is readily isolated by routine methods, and purified if desired by crystallization or chromatography over solid supports such as silica, eluting with common solvents such as ethyl acetate, acetone, and the like.

An alternative method for preparing compounds of the invention comprises reacting a sulfonate acetic acid with an amine, alcohol, or thiol in the presence of a coupling reagent such as those commonly utilized in peptide synthesis. Typical peptide coupling reagents include N,N-dicyclohexylcarbodiimide (DCC), N-ethoxycarbonyl-2-ethoxy-1,2-dihydroquinoline (EEDQ) and carbonyldiimidazole (CDI). This direct coupling reaction is preferred for preparing invention compounds in which one or both of $R_3$ and $R_4$ of Formula I are other than hydrogen. For example, a preferred class of invention compounds have the formula

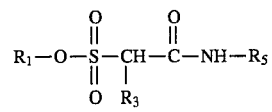

wherein $R_3$ is phenyl or naphthyl, or substituted phenyl or substituted naphthyl as defined above.

The use of a coupling reagent is depicted in Chart I, and is given in more detail in Chart II below:

CHART II

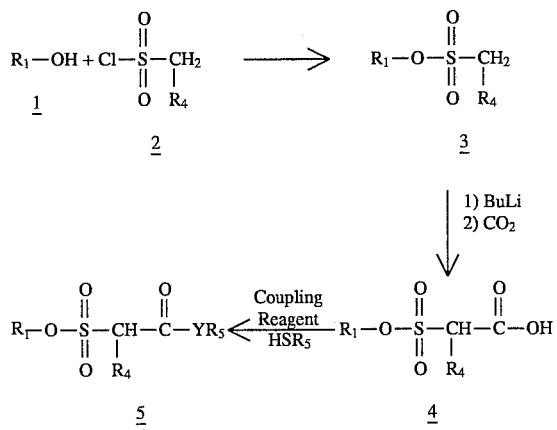

In the above Scheme II, a sulfonyl halide, such as the chloride (2), is reacted with an alcohol $R_1OH$ to give the sulfonate 3. The sulfonate is reacted with a strong base such as n-butyl lithium, generally in a solvent such as tetrahydrofuran at a reduced temperature of about −70° C., to produce a lithio salt, which generally is not isolated but is reacted directly with carbon dioxide to give the acetic acid (4). The acetic acid is reacted with an amine $H_2NR_5$, an alcohol $HOR_5$, or a thiol $HSR_5$, in the presence of a coupling reagent to afford the invention compound (5). The coupling reaction generally is conducted in an unreactive organic solvent such as dichloromethane and normally is complete in about 2 to 24 hours when carried out at about 20° C. to about 60° C. The product (5) is readily isolated by routine procedures such as filtration and evaporation of solvents, and it is further purified if desired by crystallization, chromatography, or the like.

Compounds of Formula I wherein one or both of $R_3$ and $R_4$ are other than hydrogen can alternatively be prepared simply by reacting a Formula I compound in which one or both of $R_3$ and $R_4$ are hydrogen with a strong base such as sodium hydride to form an anion, followed by reaction with a compound of the formula $R_3L$ or $R_4L$, where L is a leaving group such as halogen, especially chloro, iodo, or bromo. This reaction scheme is depicted in Chart III as follows:

CHART III

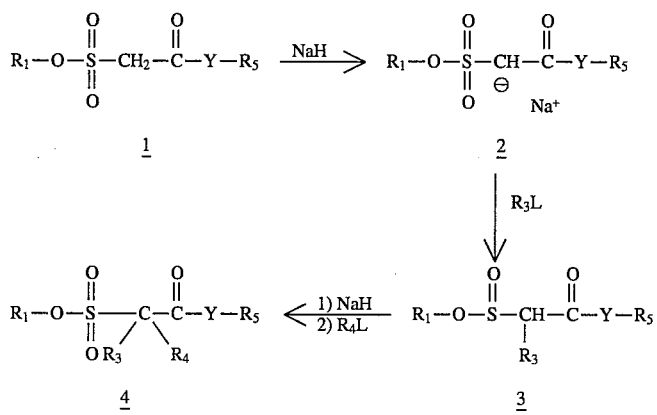

The invention compound (1) is reacted with about 1 M equivalent of sodium hydride to give anion (2), which is not isolated but rather is reacted directly with $R_3L$, for example methyl chloride, 1-naphthyl chloride, cyclopropyl iodide, phenyl iodide, or the like, to give the α-substituted sulfonamide acetic acid derivative (3). If desired, the compound (3) can be further reacted with a molar equivalent of sodium hydride, followed by reaction with $R_4L$, to give the α,α-disubstituted compound (4).

The synthesis of specific compounds provided by this invention is presented in the following detailed examples. The examples are illustrative only, and the invention is not limited to the compounds actually made or the synthetic routes utilized.

EXAMPLE 1

2,4,6-Triisopropylphenyl N,N-dibenzylcarbamoylmethylsulfonate

A. Preparation of 2,4,6-triisopropylphenoxysulfonyl acetic acid.

Sulfoacetic acid (52 g, 371 mM) and EtOH (500 mL) were heated under reflux for 20 hours. The reaction mixture was cooled, and the excess ethanol was removed under vacuum to give ethyl sulfoacetate.

$^1$H NMR (CDCl$_3$): δ1.35 (t, 3H), 4.1 (s, 2H), 4.25 (q, 2H).
A mixture of ethyl sulfoacetate (16.82 g, 100 mM) and POCl$_3$ (30.67 g, 200 mM) was heated at 125° C. for 5 hours. The mixture was cooled and filtered, and excess POCl$_3$ was removed to give ethyl chlorosulfonylacetate. The ethyl chlorosulfonylacetate (18.66 g, 100 mM) was added dropwise with stirring to a solution of 2,4,6-triisopropylphenol (22.1 g, 100 mM) in 50 mL CH$_2$Cl$_2$ maintained at 0° C. The mixture was stirred at room temperature for an additional 18 hours. The solvent was removed and the residue was redissolved in 100 mL ethyl acetate and washed with 1 N HCl and brine. The ethyl acetate was evaporated to provide ethyl (2,4,6-triisopropylphenoxysulfonyl)acetate.

This product was used for the next step without further purification.

Ethyl 2,4,6-triisopropylphenoxysulfonyl)-acetate (20 g, 52.63 mM) and KOH (3.91 g, 100 mM) were mixed in 30 mL H$_2$O and 12 mL EtOH. The mixture was stirred at room temperature until all starting material dissolved. The solvent was evaporated, and the residue was redissolved in water. The aqueous solution was washed with diethyl ether, and the aqueous portion was acidified by pH 2 by addition of 1N hydrochloric acid. The acidic solution was extracted three times with 50 mL portions of diethyl ether. The ethereal extracts were combined and the solvent was removed by evaporation to give 2,4,6-triisopropylphenoxysulfonyl acetic acid.

$^1$H NMR (CDCl$_3$): δ 1.2 (18H, d); 2.75–2.9 (1H, m); 3.2–3.35 (2H, m); 4.4 (2H, s); 6.98 (2H, s).

B. Synthesis of 2,4,6-triisopropylphenyl N,N-dibenzylcarbamoylmethylsulfonate

To a stirred solution of 2,4,6-triisopropylphenoxysulfonyl acetic acid (1.0 g, 2.92 mM) in 15 mL of methylene chloride at 0° C. was added a solution of dibenzylamine (0.59 g, 2.92 mM) and dicyclohexylcarbodiimide (0.62 g, 3 mM) in 10 mL of methylene chloride. The reaction mixture was stirred 1 hour at 0° C., warmed to 24° C., and stirred at that temperature for 12 hours. The reaction mixture was filtered to remove the solid precipitate. The filtrate was concentrated to an oil by evaporation of the solvent under reduced pressure. The oil was purified by chromatography over a silica gel column, eluting with hexane:ethyl acetate (1:1 v/v). The fractions showed by thin layer chromatography to contain the major component were combined and the solvent was removed by evaporation under reduced pressure to provide 0.5 g (76%) of 2,4,6-triisopropylphenyl N,N-dibenzylcarbamoylmethyl sulfonate, mp 107°–110° C.

EXAMPLE 2

2,4,6-Triisopropylphenyl N-diphenylmethylcarbamoylmethyl sulfonate

This compound was prepared by the procedure of Example 1, except the dibenzyl amine was replaced with diphenylmethyl amine, mp 165°–166° C.

EXAMPLE 3

2,6-Diisopropylphenyl N-dodecyl carbamoylmethyl sulfonate

The general procedure of Example I(A) was followed to react ethyl chlorosulfonylacetate with 2,6-diisopropylphenol to give ethyl (2,6-diisopropylphenoxysulfonyl)acetate. The ethyl acetate derivative was hydrolyzed to 2,6-diisopropylphenoxysulfonyl acetic acid. The acetic acid derivative was reacted with dodecylamine and DCC according to Example I(B) to provide 2,6-diisopropylphenyl N-dodecylcarbamoylmethylsulfonate, mp 75°–78° C.

EXAMPLE 4

2,6-Diisopropylphenyl N-diphenylmethylcarbamoylmethyl sulfonate

This compound was prepared by following the general procedure of Example 3, except the dodecyl amine was replaced with diphenylmethyl amine, mp 120°–122° C.

EXAMPLE 5

2,6-Diisopropylphenoxysulfonyl acetic acid

This compound was described in experimental section of Example 3.

$^1$H NMR (CDCl$_3$: δ1.12 (12H, d), 3.15–3.22 (2H, m), 4.22 (2H, s), 7.08–7.15 (3H, m), 9.4 (1H, br).

EXAMPLE 6

2,6-Diisopropylphenyl N-(2,3,6-triisopropylphenyl)carbamoylmethylsulfonate

This compound was prepared by the same procedure of Example 3, except the dibenzyl amine was replaced with 2,4,6-triisopropylaniline, mp 211°–213° C.

EXAMPLE 7

2,4,6-Triisopropylphenyl N-isopropyl-N-(4-thiomethylphenylmethyl)carbamoylmethyl sulfonate This compound was prepared in the same manner as for the title compound of Example 1, except the dibenzyl amine was replaced with N-isopropyl-N- (4-thiomethylphenyl)methyl) amine, mp 110°–112 ° C.

EXAMPLE 8

2,6-Diisopropylphenyl (2,6-diisopropylphenoxycarbonyl)methylsulfonate 2,6-Diisopropylphenoxysulfonyl acetic acid (prepared as described in Example 3) was reacted with oxalyl chloride to provide 2,6-diisopropylphenoxysulfonyl acetyl chloride. The acid chloride was reacted with 2,6-diisopropylphenol in dichloromethane to provide, following evaporation of the reaction solvent, 2,6-diisopropylphenyl (2,6-diisopropylphenoxycarbonyl)methyl sulfonate, mp 90°–92° C.

EXAMPLE 9

3,4,6-Triisopropylphenyl N-(2.6-diisopropylphenyl)carbamoylethyl sulfonate

This compound was prepared by the procedure of Example 1, except the dibenzyl amine was replaced with 2,6-diisopropylaniline, mp 193°–195° C.

EXAMPLE 10

2.6-Diisopropylphenyl N-(2,6-diisopropylphenyl)carbamoylmethylsulfonate

This compound was prepared by the general procedure of Example 3, except the dibenzyl amine was replaced with 2,6-diisoproylaniline, mp 178°–180° C.

Additional compounds which can be prepared utilizing the general methods described above include:

3-cyano-4-trifluoromethylphenyl (2-chloro-3-nitrophenylthiocarbonyl)methyl sulfonate;

2-naphthyl N-isobutyl-N-(n-octyl)carbamoylmethyl sulfonate;

(3-hydroxy-5-iodo-7-carboxy)naph-2-yl phenylthiocarbonylmethyl sulfonate;

4-methoxy-2-pyridyl dodecylthiocarbonylmethyl sulfonate;

1-n-propylpyrazol-4-yl N,N-dibenzylcarbamoylmethyl sulfonate;

2,4,6-triethoxyphenyl N-(3,4-dichlorophenylmethyl)carbamoylmethyl sulfonate;

3-methyl-2-pyridyl dodecylthiocarbonylmethyl sulfonate;

cyclopropyl N-(phenylmethyl)carbamoyl sulfonate;

4-octylphenyl (3-phenylbutoxycarbonyl)methyl sulfonate;

2-cyanophenyl N-isoheptyl-N-(3-bromophenylmethyl)carbamoylmethyl sulfonate;

2,4,6-triisopropylphenyl 1-methyldodecylthiocarbonylmethyl sulfonate;

2,4,6-triisopropylphenyl 2,6-diisopropylphenylthiocarbonyl sulfonate;

3-methyl-4-ethyl-1-pyridyl dodecylthiocarbonylmethyl sulfonate;

4-(2-chlorophenyl)-5,7-dimethylquinolin-2-yl N-methyl-N-(2-chlorophenylmethyl)carbamoylmethyl sulfonate;

4,6-dimethyl-5-pyridinyl methylthiocarbonylmethyl sulfonate;

4-(2-chlorophenyl)-5,7-dimethylquinolin-2-yl 1-(methoxycarbonyl)ethyl sulfonate; 4-trifluoromethylphenyl 1-[N-n-hexyl-N-(3-chlorophenylmethyl)carbamoyl]-3-phenylpropyl-1-sulfonate;

3-aminomethylphenyl dodecyloxycarbonylmethyl sulfonate;

4-ethoxycarbonylphenyl N-methyl-N-tetradecylcarbamoylmethyl sulfonate;

6-nitro-1-naphthyl 3-(4-nitrophenyl)-hexylthiocarbonylmethyl sulfonate;

5,7-dimethylnaphthylridin-2-yl tert.-butoxycarbonylmethyl sulfonate;

4-(3-phenylpropylthio)-2-pyridyl (2-methyl-3-chloro-5-nitrophenylthio) carbonylmethyl sulfonate;

2-n-butylphenyl N-(dec-3-ene-1-yl)carbamoylmethyl sulfonate;

4-hydroxyphenyl 3-(methoxycarbonylphenylmethoxy)carbonylmethyl sulfonate;

4-methoxycarbonylphenyl N-(3-cyanophenyl)-N-(2,3-diiodophenylmethyl)carbamoylmethyl sulfonate;

4-aminophenyl N-(4-aminophenylmethyl)carbamoyl sulfonate dihydrochloride;

3-cyano-4-nitrophenyl (3,5-diaminophenylmethoxy)carbonylmethyl sulfonate diacetate; and 3,5 -diisobutylphenyl N-[2-(3-chlorophenyl)propylcarbamoyl sulfonate.

The compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia and atherosclerosis, and in general lipid regulation.

The ability of representative compounds of the present invention to inhibit ACAT was measured using an in vitro test more fully described in F.J. Field and R.G. Salone, *Biochemica et Biophysica Acta,* 772:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rat liver microsomes (designated LAI).

These data appear in Table 1 where they are expressed as $IC_{50}$ values; i.e., the micromolar concentration of test compound required to inhibit the activity of the enzyme by 50%.

In an in vivo screen designated APCC, male Sprague-Dawley rats (200–225 g body weight) were randomly divided into treatment groups and dosed at 4 PM with either vehicle (CMC/Tween) or suspensions of invention compounds in vehicle. The normal chow diet was then replaced with a high fat, high cholesterol diet (5.5% peanut oil, 1.5% cholesterol, and 0.5% cholic acid). The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention also appear in Table I as the percent change in total cholesterol (%TC) from control animals given vehicle and diet only. All compounds in the APCC test reported in Table 1 were administered by gavage at 30 mg/kg.

TABLE I

| Example | Structure | LAI | APCC |
|---|---|---|---|
| 1 | 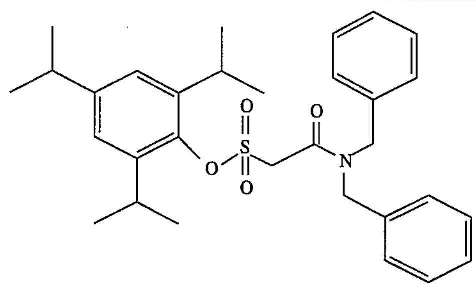 | >5.0 | −7 |
| 2 | 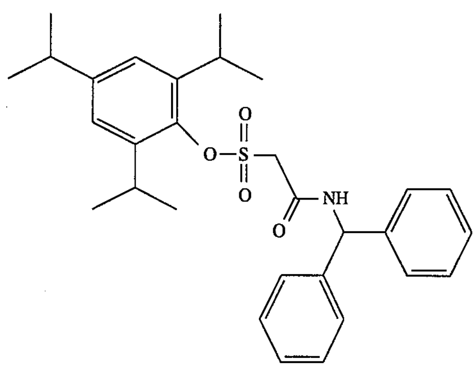 | 0.79 | −19 |
| 3 | 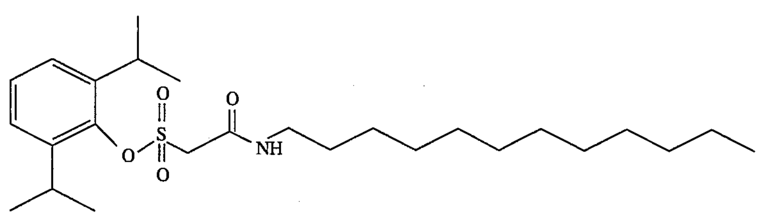 | 3.0 | −3 |
| 4 | 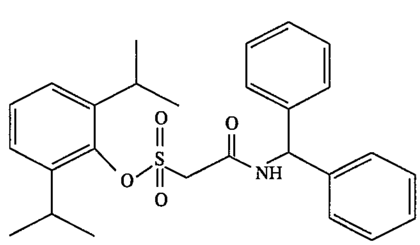 | 1.8 | −43 |

TABLE I-continued

| Example | Structure | LAI | APCC |
|---|---|---|---|
| 5 | 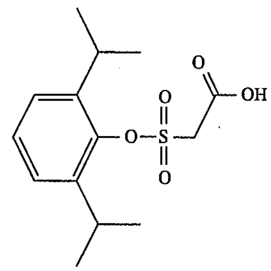 | >50.0 | −31 |
| 6 | 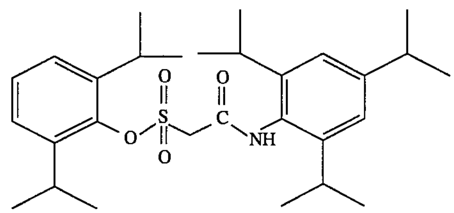 | 1.66 | −31 |
| 7 | 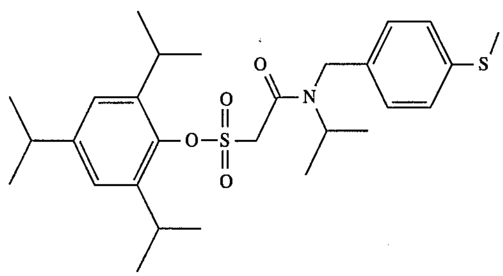 | 3.6 | −17 |
| 8 | 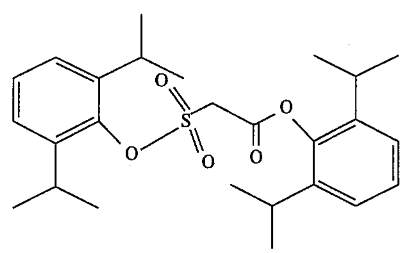 | 1.5 | −21 |
| 9 | 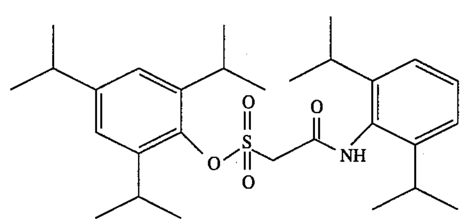 | 0.007 | −61 |
| 10 | 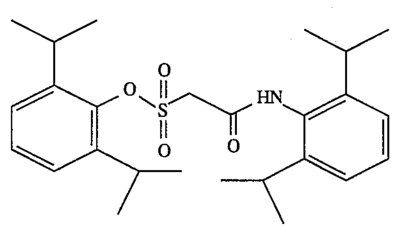 | 0.027 | −42 |

In therapeutic use as agents for treating hypercholesterolemia or atherosclerosis, the compounds of Formula I or pharmaceutically acceptable salts thereof are administered to the patient at a dosage which is effective in inhibiting ACAT. Such ACAT-inhibiting levels generally are from about 50 to about 3000 mg per day, ideally from about 100 to about 1000 mg per day. For a normal human adult of approximately 70 kg of body weight, a typical dosage of from about 1 to about 40 mg/kg of body weight per day will be utilized. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner, cachets are also included.

Tablets, powders, cachets, and capsules can be used as solid dosage forms suitable for oral administration. Sustained-release formulation can be prepared utilizing conventional techniques such as polymers, osmotic pumps, wax, and the like.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The following examples further illustrate typical pharmaceutical formulations provided by this invention.

EXAMPLE 11

A pharmaceutical formulation in the form of hard gelatin capsules for oral administration are prepared using the following ingredients:

|  | Quantity (mg/capsule) |
| --- | --- |
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is 2,6-diisopropylphenyl N-(2-methyl-3-bromophenylmethyl)carbamoylmethyl sulfonate.

EXAMPLE 12

| Formulation for Oral Suspension | |
| --- | --- |
| Ingredient | Amount |
| 1-Naphthyl N-(n-octyl)carbamoylmethyl sulfonate | 500 mg |
| Sorbitol solution (70% N.F.) | 40 mL |
| Sodium benzoate | 150 mg |
| Saccharin | 10 mg |
| Cherry flavor | 50 mg |
| Distilled water q.s. ad | 100 mL |

The sorbitol solution is added to 40 mL of distilled water and the tetrazole acetamide is suspended therein. The saccharin, sodium benzoate, and flavoring are added and dissolved. The volume is adjusted to 100 mL with distilled water. Each milliliter of syrup contains 5 mg of active ingredient.

EXAMPLE 13

Tablets each containing 60 mg of active ingredient.

| | |
| --- | --- |
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1.0 mg |
| Total | 150 mg |

The active ingredients, starch and cellulose, are passed through a No. 45 mesh U.S. sieve and mixed thoroughly. The solution of polyvinylpyrrolidone is mixed with the resultant powders and then passed through a No. 14 mesh U.S. sieve. The granules are dried at 50°–60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 1.

EXAMPLE 14

A parenteral composition suitable for administration by injection is prepared by dissolving 100 mg of 3-trifluoromethylphenyl phenoxycarbonylmethyl sulfonate in 250 mL of 0.9% aqueous sodium chloride solution and adjusting the pH of the solution to about 7.0.

EXAMPLE 15

Preparation for Suppositories

A mixture of 500 mg of 2,4,6-trichlorophenyl (n-dodecylthiocarbonyl)methyl sulfonate and 1500 mg of theobroma oil are blended to uniformity at 60° C. The mixture is cooled to 24° C. in tapered molds. Each suppository will weight about 2 g and can be administered from 1 to 2 times each day for regulation of lipids and treatment of hypercholesterolemia.

What is claimed is:

1. A compound of Formula I

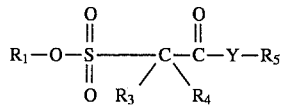

wherein $R_1$ is selected from (a) phenyl substituted with from 1 to 3 substituents selected from $C_1$–$C_4$ alkyl, $C_1$–$C_4$ alkoxy, $C_1$–$C_4$ alkylthio, hydroxy, halo, nitro, cyano, trifluoromethyl,

-COOH,

-COOalkyl wherein alkyl has from 1 to 4 carbon atoms and which is straight or branched, -$(CH_2)_m NR_x R_y$ wherein m is 0 or 1, and each of $R_x$ and $R_y$ is independently hydrogen or $C_1$–$C_4$ alkyl;

$R_3$ and $R_4$ independently are $C_3$–$C_6$ cycloalkyl, hydroxy-$C_1$–$C_4$ alkyl, $C_1$–$C_4$ alkoxy, hydrogen, $C_1$–$C_4$ alkyl, phenyl, 1- or 2-naphthyl, or phenyl or naphthyl substituted with from 1 to 3 substituents selected from $C_1$–$C_4$ alkyl, $C_1$–$C_4$ alkoxy, $C_1$–$C_4$ alkylthio, halo, nitro, cyano, trifluoromethyl, phenyl, or $C_3$–$C_8$ cycloalkyl; or $R_3$ and $R_4$ taken together with the carbon to which they are attached complete a $C_3$–$C_8$ carbocyclic ring;

Y is -$NR_2$-, wherein $R_2$ is hydrogen $C_1$–$C_4$ alkyl, phenyl, $C_1$–$C_4$ alkylphenyl, wherein the phenyl may be substituted with 1, 2, or 3 groups selected from $C_1$–$C_4$ alkyl, $C_1$–$C_4$ alkoxy, $C_1$–$C_4$ alkylthio. hydroxy, halo, nitro, cyano, trifluoromethyl, and COOH;

$R_6$ is phenyl substituted with from 1 to 3 substituents selected from:

$C_1$–$C_4$ alkyl, $C_1$–$C_4$ alkoxy, $C_1$–$C_4$ alkylthio, phenyl, hydroxy, halo, nitro, cyano, trifluoromethyl,

-COOH,

-COOalkyl wherein alkyl has from 1 to 4 carbon atoms and which is straight or branched, and -$(CH_2)_m NR_x R_y$, wherein m is 0 or 1, and each of $R_x$ and $R_y$ is hydrogen or a straight chain alkyl group having 1 to 4 carbon atoms.

2. A compound of claim 1 having Formula II

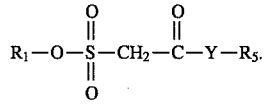

3. A compound of claim 2 wherein $R_x$ is phenyl substituted with 1, 2 or 3 substituents selected from $C_1$–$C_4$ alkyl and $C_1$–$C_4$ alkoxy.

4. A compound of claim 2 wherein $R_6$ is phenyl substituted with 1, 2, or 3 substituents selected from $C_1$–$C_4$ alkyl or $C_1$–$C_4$ alkoxy.

5. The compound of claim 2 which is 2, 6-Diisopropylphenyl N-(2,3,6-triisopropyl-phenyl) carbamoylmethylsulfonate;

2,4,6-Triisopropylphenyl N-(2,6-diisopropylphenyl)carbamoylmethyl sulfonate; and 2,6-Diisopropylphyenyl N-(2,6-diisopropyl-phenyl)carbamoylmethylsulfonate.

6. A pharmaceutical formulation for treating hypercholesterolemia or atherosclerosis comprising an ACAT-inhibiting amount of a compound of claim 1 together with a pharmaceutically acceptable carrier, diluent, or excipient therefor.

7. A formulation of claim 6 employing a compound of the formula

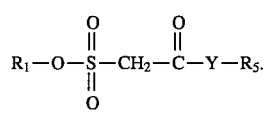

8. A formulation of claim 7 employing a compound wherein $R_1$ is phenyl substituted with 1, 2, or 3 groups selected from $C_1$–$C_4$ alkyl and $C_1$–$C_4$ alkoxy.

9. A formulation of claim 8 wherein $R_6$ is phenyl substituted with 1, 2, or 3 groups selected from $C_1$–$C_4$ alkyl and $C_1$–$C_4$ alkoxy.

10. A method of treating hypercholesterolemia or atherosclerosis comprising administering to a mammal in need of such treatment an ACAT inhibiting amount of a compound of claim 1.

11. A method of claim 10 employing a compound of the formula

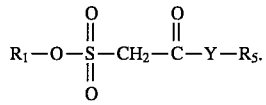

12. A method according to claim 11 employing a compound where $R_1$ is phenyl substituted with 1, 2, or 3 groups selected from $C_1$–$C_4$ alkyl and $C_1$–$C_4$ alkoxy.

13. A method according to claim 12 employing a compound wherein $R_5$ is phenyl substituted with 1, 2, or 3 groups selected from $C_1$–$C_4$ alkyl and $C_1$–$C_4$ alkoxy.

* * * * *

UNITED STATES PATENT AND TRADEMARK OFFICE
CERTIFICATE OF CORRECTION

PATENT NO. : 5,510,379
DATED : April 23, 1996
INVENTOR(S) : Helen T. Lee et al.

It is certified that error appears in the above-indentified patent and that said Letters Patent is hereby corrected as shown below:

Column 21, line 55, "$R_6$" should read -- $R_5$ --.

Column 22, line 15, "$R_x$" should read -- $R_1$ --.

Column 22, line 18, "$R_6$" should read -- $R_5$ --.

Column 22, line 44, "$R_6$" should read -- $R_5$ --.

Signed and Sealed this

Twenty-seventh Day of March, 2001

Attest:

NICHOLAS P. GODICI

*Attesting Officer*   *Acting Director of the United States Patent and Trademark Office*